United States Patent
Yan et al.

(10) Patent No.: US 10,654,974 B2
(45) Date of Patent: May 19, 2020

(54) BONE REPAIR MATERIAL OF MULTIVARIANT AMINO ACID POLYMER-HYDROXYAPATITE, SUPPORTIVE IMPLANTS AND THE PREPARATION METHOD THEREOF

(71) Applicant: SICHUAN NATIONAL NANO TECHNOLOGY CO., LTD, Chengdu, Sichuan (CN)

(72) Inventors: YongGang Yan, Sichuan (CN); HaoHao Ren, Sichuan (CN); PengZhen Liu, Sichuan (CN); Hong Li, Sichuan (CN); GuoYu Lv, Sichuan (CN); Fan Xu, Sichuan (CN); Peng Wang, Sichuan (CN); XinYan Hao, Sichuan (CN); XiaoXia Fan, Sichuan (CN)

(73) Assignee: SICHUAN NATIONAL NANO TECHNOLOGY CO., LTD, Chengdu, Sichuan (CN)

( * ) Notice: Subject to any disclaimer, the term of this patent is extended or adjusted under 35 U.S.C. 154(b) by 230 days.

(21) Appl. No.: 15/524,491

(22) PCT Filed: Jan. 30, 2015

(86) PCT No.: PCT/CN2015/071967
§ 371 (c)(1),
(2) Date: May 4, 2017

(87) PCT Pub. No.: WO2016/070501
PCT Pub. Date: May 12, 2016

(65) Prior Publication Data
US 2017/0327643 A1    Nov. 16, 2017

(30) Foreign Application Priority Data

Nov. 4, 2014 (CN) .................. 2014 1 06127434

(51) Int. Cl.
| | |
|---|---|
| *C08G 69/08* | (2006.01) |
| *A61L 27/46* | (2006.01) |
| *C08G 69/10* | (2006.01) |
| *A61L 27/12* | (2006.01) |

(52) U.S. Cl.
CPC .............. *C08G 69/08* (2013.01); *A61L 27/12* (2013.01); *A61L 27/46* (2013.01); *C08G 69/10* (2013.01); *A61L 2430/02* (2013.01)

(58) Field of Classification Search
CPC .......... A61K 35/32; A61L 27/12; C08G 69/08
See application file for complete search history.

(56) References Cited

FOREIGN PATENT DOCUMENTS

| | | |
|---|---|---|
| CN | 101342384 A | 1/2009 |
| CN | 101716377 A | 6/2010 |
| CN | 101716378 A | 6/2010 |
| CN | 101342383 B | 9/2011 |
| WO | 2003049780 A1 | 6/2003 |

OTHER PUBLICATIONS

Li et al (Degradable biocomposite of nano calciumdeficient hydroxyapatite-multi(amino acid) copolymer, International Journal of Nanomedicine 2012:7 1287-1295), Jul. 2012.*
Bianco et al (Electrospun poly(ε-caprolactone)/Ca-deficient hydroxyapatite nanohybrids: Microstructure, mechanical properties and cell response by murine embryonic stem cells, Materials Science and Engineering C 29 (2009) 2063-2071), Sep. 2009.*
Qi et al (Development and characterization of an injectable cement of nano calcium-deficient hydroxyapatite/ multi(amino acid) copolymer/ calcium sulfate hemihydrate for bone repair, International Journal of Nanomedicine 2013:8 4441-4452), published on Nov. 2013.*

* cited by examiner

*Primary Examiner* — Gregory Listvoyb
(74) *Attorney, Agent, or Firm* — Novick, Kim & Lee, PLLC; Allen Xue

(57) ABSTRACT

The present invention relates to bone repair material of multivariant amino acid polymer-hydroxyapatite, supportive implants and preparation method. Said restorative material is made of multivariant amino acid polymers consisted with ε-aminocaproic acid and other α-amino acids, together with constituents modified hydroxyapatite, in which the constituent modified hydroxyapatite uses calcium salt as modified constituents that can be accepted in medicine and has a more solubility compared with hydroxyapatite. Modified hydroxyapatite is constructed from said calcium salt and hydroxyapatite, with a mass ratio of (2-20):(98-80), and the content of modified hydroxyapatite is 10-70% based on the mass of said bone repair material; the content of ε-aminocaproic acid in multivariant amino acid polymers is 60-99% based on the total molar quantity of multivariant amino acid polymers.

6 Claims, 1 Drawing Sheet

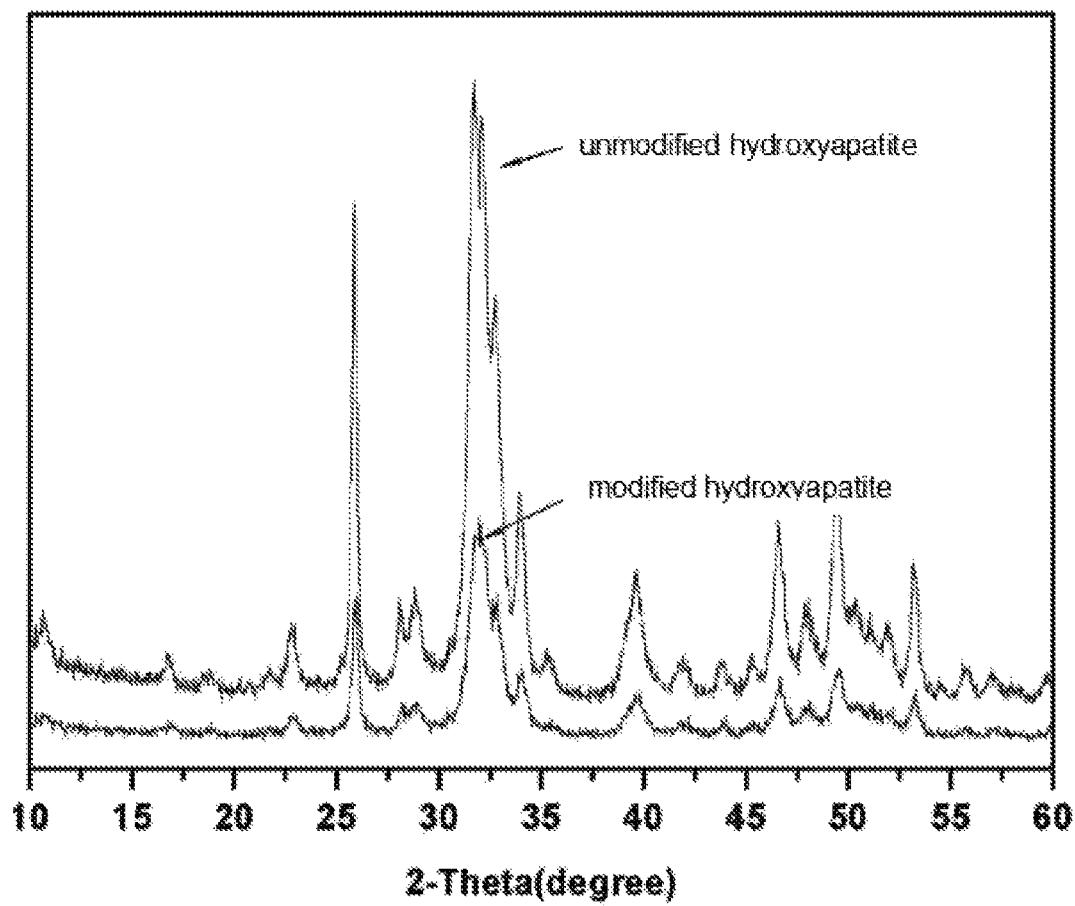

BONE REPAIR MATERIAL OF MULTIVARIANT AMINO ACID POLYMER-HYDROXYAPATITE, SUPPORTIVE IMPLANTS AND THE PREPARATION METHOD THEREOF

TECHNICAL FIELD

The present invention relates to a medically acceptable bone repair material, corresponding bone repair products, and the preparative method thereof, especially the bone repair material of multivariant amino acid polymer-hydroxyapatite, corresponding supportive bone implant and the preparative method thereof.

BACKGROUND ART

The bone tissue repair products used in clinical may include two types, i.e. the filled type and the supportive type. The filled bone repair material is mainly used for filled implant after cut due to trauma, tumor, and tubercle, etc; the supportive bone repair material can provide the fundamental mechanical supportive requirements, and be used as implants for bone defect repair resulted from pathological change in backbone, four limbs, head, etc or from external injury.

For supportive bone repair material, providing the necessary fundamental mechanical support in implant sites is a important basic function and currently, the metal and synthetic materials are mainly used. In recent years, polymers have been widely used in hard tissue damage of human body, as well as repair and restoration of disease, and have shown excellent performance, such as PEEK (ploy(etherether-ketone)) is regarded as having good biomechanics-compatible substitution material of hard tissue and widely used in spinal repair and correction, etc; UHMWPE (ultra-high molecular weight polyethylene) has a wide application in artificial joint. Like PEEK and UHMWPE, most of the non-degradation polymers including most of strong intensity materials such as polyethylene, polypropylene, polyacrylic ester, aromatic acid, polysiloxane, polyformaldehyde and so on, are all bioinert materials with good physical mechanical property. The materials can keep long-term stabilization, without degradation and cross-linking, etc, and are generally implanted in body for a long time and used in the stable bearing sites. But for the materials cannot fully fuse with bone tissue, the function in repair and reconstruction of hard tissues is limited. The composite material of nano-hydroxyapatite/polyamide (nHA/PA66) is a bone supportive repair material currently used in clinical, and has good biocompatibility, bioactivity, biosafty, and shows a good clinical effect on repair and substitution of weight-bearing bonds such as cervical vertebra, thoraco-lumbar vertebra, etc. The composite material is hard to degradation, and suitable for the long-term implant application in support sites.

Content of the Invention

Based on above conditions, the present invention provides a new type of bone repair material of multivariant amino acid polymer-hydroxyapatite, and there is a micro-degradation on the surface of material in body, and rapidly release calcium/phosphorous ions, and possess higher retention of mechanical strength. The present invention further provides corresponding supportive complex bone implants, together with the preparative method thereof.

Since natural bone is a natural nanometer complex structure formed by weakly crystallized hydroxyapatite and collagen; bone collagen is a high polymer multi-dimensional structure consisted with natural amino acid by specific systematic arrangement, therefore materials similar to bone tissue are obtained by synthesizing amino acid polymers having similar composition and structure to collagen structure of human body, and compounding the polymers and modified HA, which provides evidences for preparing supportive complex bone implant.

Bone repair material of multivariant amino acid polymer-hydroxyapatite according to the present invention is constituted from multivariant amino acid polymer (consisted with ε-aminocaproic acid and other α-amino acids) and the constituent modified hydroxyapatite, in which the constituent hydroxyapatite is the modified hydroxyapatite composed of said calcium salts as modified constituents and hydroxyapatite, and said calcium salts can be accepted in medicine and have a better solubility than that of hydroxyapatite, wherein:

For modified hydroxyapatite, the mass ratio of said modification constituents calcium salts and hydroxyapatite is (2-20):(98-80), and preferably the mass ratio is (5-15):(95-85);

The mass of modified hydroxyapatite is 10-70% based on the mass of said bone repair material, and preferably is 25-55%;

The content of ε-aminocaproic acid in multivariant amino acid polymers is 60-99% based on the total molar quantity of multivariant amino acid polymers, and preferably is 85-95%, and the remaining is other amino acids.

In above modified hydroxyapatite, it is preferable for said calcium salts used for modification to get into the crystal lattice of hydroxyapatite by ion exchange and in situ dispersion polymerization and so on. On the basis of still keeping the elementary structure of hydroxyapatite, the modified calcium salts enter the lattice and result in the instability of the crystal structure, and then the solubility is increased, that is beneficial for the rapid release of calcium/phosphorus ions and the surface activity. Thus, if the usage amount of said modified calcium salt is too low, the modified effect can be affected.

The experiment shows that the releasing concentration of calcium/phosphorus ions for modified hydroxyapatite may increase 1-3.5 times compared with that of unmodified, which is beneficial for the fast healing of bone tissue.

In order to obtain hydroxyapatite of fast releasing calcium/phosphorus ions, said medically acceptable calcium salts used for modification generally include but are not limited to at least one of common calcium salts such as calcium hydrogen phosphate ($CaHPO_4 \cdot 2H_2O$), calcium biphosphate ($Ca(H_2PO_4)_2 \cdot H_2O$), calcium sulfate ($CaSO_4$), calcium citrate ($(C_6H_5O_7)_2Ca_3 \cdot 4H_2O$) and calcium glycerophosphate ($C_6H_{14}Ca_2O_{12}P_2$).

The investigation has already indicated that although synthetic polyamide PA-66 cannot be degraded by esterase, it can be degraded by papain, trypsinase, and chymotrypsin, while the degradation level is very low, in which lignin-degrading strains have a low degree of degradation for PA-66. It is difficult for the polyamide 6 formed by polymerization of 6-aminocaproic acid to be degraded, and only oligomers with a polymerization degree ≤6 can be degraded by flavobacterium strains (K172 P-E I, F-E II, E III), pseudomonas strains NK87 (P-E II), and 6-aminocaproic acid oligomer hydrolase (E-III). But in nature, biosynthetic proteins and polypeptide silk, collagen, which all contain the structure of of PA, can be biodegradable. Thus, controlling the composition and structure of ployamino acid is the key to obtain the copolymer of multivariant amino acids with surface degradation efficiency.

The multivariant amino acid polymer described in above bone repair material of the present invention constituted by ε-aminocaproic acid and other α-amino acids can be prepared by reference to those reported/used methods including the invention disclosure number CN101342383 entitled "Polymer-type tissue repair material and the preparative method thereof" applied by the inventors. Amongst, except for ε-aminocaproic acid, said α-amino acids can be preferably selected from weakly alkaline or neutral amino acids, such as glycine, alanine, leucine, isoleucine, valine, cystine, cysteine, methionine, threonine, serine, phenylalanine, tyrosine, tryptophan, proline, methionine and hydroxyproline, lysine, arginine, histidine and so on. In human body, said polymer can be degraded gradually, and the half life of degradation can be adjusted by the ratio of ε-aminocaproic acid, and part of the degradation products is the essential components for the human body's protein composition, thus can overcome the uncontrollable degradation of current complex biomaterials and/or harmful irritant reaction caused by the degradation process and the degradation products or the defects including unconnected with tissues resulted from non-degradable and so on.

The investigation showed that the degradation patterns of degradable materials may include two major categories, i.e. noumenon degradation and surface corrosion degradation, based on the difference between the chain-breaking speed of molecular chain in the structure of materials due to attack of water and enzyme, and the speed that water molecules or enzyme molecules get into the interior of materials. When the chain-breaking speed of material molecules is lower than the speed that the molecules of water and enzyme enter, the surface molecule chain and the inner molecules of materials can break together, and be shown as noumenon degradation. On the contrary, when the chain-breaking speed of molecule chains is higher than the speed of water and enzyme enter into the interior of materials, the breaking of molecule chains are mainly found on the surface of materials, and thus represents the surface corrosion degradation.

As the degradation of materials, their own mechanical strength is generally lost. For the noumenon degradation materials, due to the simultaneously break of inner and exterior molecule chains, the mechanical efficient of materials has a rapid decrease at the initial stage of degradation, and as the elongation of degradation time, materials all change into low molecular compounds, become colloidal state, and can not provide any mechanical support. Thus, said materials are not suitable for the supportive bone implant. For the materials of surface corrosion degradation, because the chain-breaking mainly occurs on the surface of materials, the materials can still remain higher mechanical strength. Experimental results show above bone repair materials of the present invention and their corresponding products including supportive complex bone implant and so on only have 330 wt %, even only 5-15 wt % of weight loss caused by surface micro-corrosion degradation in tissue fluid in body. Obviously, materials of surface corrosion degradation are an ideal choice for supportive bone repair implant.

For the preparation of above bone repair material of multivariant amino acid polymer-modified hydroxyapatite according to the present invention, the elementary process is as follows: under inactive gas protection, said modification constituent calcium salts, hydroxyapatite, ε-aminocaproic acid, and other amino acid monomers are added to water, and allow amino acids dissolve in water and form the solution of amino acids, while slightly soluble or soluble calcium salts as modification constituents and hydroxyapatite, with relatively higher dissolubility, can carry out ion exchange through surface; and the mixture is gradually warmed to 150-180° C. under stirring, following by mixing and dehydrating (it should be noted that slowly warming is better, such as the temperature is raised at a rate of 5-10° C./min, so as to have a gradual dehydration); the mixture is then continually heated to the molten state of 280° C., to carry out the in situ polymerization and complex reaction and obtain said bone repair material of multivariant amino acid polymer-modified hydroxyapatite. Wherein, the better temperature conditions are 180-260° C. for said in situ polymerization reaction. In order to be more advantageous for the polymerization reaction to be gradually and mildly carried out, and to ensure the quality of products, the rate speed is 5-10° C./min for said warming after dehydration is also preferable.

One the basis of above elementary process, further preferable way is that said in situ polymerization reaction can be carried out by two steps: the dehydrated mixture material is subjected to the first step of in situ polymerization and complex reaction for 2-5 h at 200-230° C., then heated to –260° C. and keep the second step of polymerization reaction for 2-5 h, to provide said bone repair material after completion of reaction and cooling.

Using above bone repair material of multivariant amino acid polymer-hydroxyapatite according to the present invention as raw materials, and by processing with general injection molding, the supportive complex bone implant can be prepared, having suitable shapes in need and practical uses. For example, the implant can be a solid cylinder with a diameter of 2-50 mm and a height of 5-150 mm, or a hollow cylinder with an inner diameter of 2-50 mm, an outer diameter of 5-600 mm, and a height of 4-150 mm, or a cube with a side length of 2-150 mm, or a trapezoid piece with a upper/lower line of respective 1-28 mm/5-30 mm, and other irregular shapes (such as various kinds of shapes humanoid bone tissues including H shape repairing lamina of vertebra, Y shape, arch shape, etc).

For said process of injection molding, in general, carrying out at a temperature of 160-280° C. and under a pressure of 40-180 MPa are all permitted, and further preferable way of injection molding can choose to perform at a temperature of 180-240° C. and/or under a pressure of 80-150 MPa. The experiment shows the change of temperature and/or pressure in said range generally can not affect the performance of obtained products.

In addition, when said injection molding is carried out, using granular bone repair materials of multivariant amino acid polymer-modified hydroxyapatite with a diameter of 1-5 mm as raw materials is a preferred choice.

Experimental results show that for the supportive complex bone implant obtained by above process of the present invention, not only its compressive strength can reach 95-150 MPa, generally >120 MPa, while bending strength generally ≥70 MPa (up to 70-130 MPa), but also when its compressive migration is 0.6 mm, the compressive strength is not less than 3 KN, similar to mechanical properties of bearing position of human bone. At the same time, after implanted in body, the weight loss due to surface micro-degradation under action of tissue fluid is the same as described above, and generally can reach 3-30 wt %, and better weight loss caused by micro-degradation can be 5-15 wt %. During the process of preparation, changing the time of polymerization reaction and/or adjusting the molecular weight of raw materials can realize the adjustment of degradation ratio, and thus realize the rapid release and supply of calcium/phosphorus ions required for bone tissue repair, facilitating the fast healing of bone tissue, while can also steadily keep enough mechanical strength required, satisfying the basic need for mechanical support during tissue healing.

According to the actual demand, the above bone repair material of multivariant amino acid polymer-modified hydroxyapatite, by adjusting and changing the ratio of said contituents multivariant amino acid polymer and modified hydroxyapatite and/or the ratio of ε-aminocaproic acid and other α-amino acids in multivariant amino acid polymer and/or the polymerization degree of multivariant amino acid polymer during preparation and reducing the ratio of modified hydroxyapatite and/or increasing the molecular weight of multivariant amino acid polymer and similar ways can also improve the mechanical strength of supportive bone repair composite materials. Those methods are convenient, and the material can fit for repairing different parts of bone tissues, so it is an ideal supportive bone repair materials/implant products that can have a wide serviceable range.

Hereinafter, the above content of present invention can further be illustrated in detail, combined with figure and examples. But it should not be understood that above subject scope of the present invention is only limited to the following examples. Without departing from above technical spirit of the present invention, various alternations and changes that can be made by common technical knowledge in the field and commonly-used means should all be within the scope of the present invention.

DESCRIPTION OF FIGURE

The FIGURE is the XRD pattern of modified hydroxyapatite material and unmodified hydroxyapatite material.

EXAMPLE

Example 1

ε-Aminocaproic acid, alanine, phenylalanine, proline, hydroxyproline, lysine, calcium sulphate dihydrate, and hydroxyapatite were respectively taken out 122.5 g, 0.9 g, 0.8 g, 1.2 g, 4 g, 1.5 g, 13 g, 63.4 g, and added to 250 ml three-necked bottle, following by addition of 70 ml distilled water, to which nitrogen was purged for protection. Under stirring, the mixture was gradually warmed to 150-180° C. at a rate of 5-10° C./min and slowly dehydrated (about 70 ml water being deprived), and then continued to gradually heat to 210° C. for melting, and at 220° C., the in situ polymerization and complex reaction was successively carried out for 3.5 h and ceased. Under the protection of nitrogen, the reaction mixture was cooled to ambient temperature, to obtain bone repair materials of multivariant amino acid polymer-modified hydroxyapatite, with a yield of 91.2%. The obtained composite material was crushed into particles with diameter 15 mm, and the content of inorganic substance was detected by burning at 800° C. The content of inorganic substance in composite materials was 39.5%, in which the content of calcium sulfate was 5.5%, and the content of hydroxyapatite was 34%.

Above granular composite material was injection-molded as normal sample belt (i.e. supportive complex bone implant) at a temperature of 160-250° C. and under a pressure of 60-150 MPa, and the compressive strength of standard sample belt was measured as 143 MPa and the bending strength as 85 MPa. Under said injection-moulding conditions, the composite material was injection-molded into the lumbar vertebrae support of 24×12×10 (ie. supportive complex bone implant), with a compressive strength of up to 10480 N (3 mm deformation).

The supportive complex bone implant of multivariant amino acid polymer-modified hydroxyapatite (test sample) was subjected to degradation and bioactive test in simulated body fluid, using the supportive complex implant of multivariant amino acid polymer-hydroxyapatite containing a same ratio of hydroxyapatite as reference. After soaking for 12 weeks, the calcium ion concentration of experimental sample was 2.3 times that of the reference, while the phosphorus ion concentration of experimental sample was 2.1 times that of the reference; analysis of superficial deposit showed that after the experimental sample was soaked for three days, the surface of sample was covered by apatite sediments, but for the reference, it was seven days. The results showed the experimental sample has higher releasing concentration of calcium/phosphorus ions and more surface active sites, and said sites are the keys for the formation of apatite. For the degradation, the experimental sample lost 8% of total weight in the previous four weeks, then it maintained stable. After becoming stable, the compressive strength remained 85%, fully complying with the replacement and repair requirements of chest/lumbar vertebrae for human body.

The XRD spectra of modified hydroxyapatite materials using the method of present invention and unmodified common hydroxyapatite materials were performed and shown in the FIGURE. In the spectrum, 2-Theta=25.7, 31.8 are the characteristic peaks of hydroxyapatite. As shown in FIGURE, the crystallinity degree of hydroxyapatite modified by the method of present invention was obviously lower than that of unmodified hydroxyapatite, indicating calcium sulphate dehydrate used for modification got into crystal lattices of hydroxyapatite, significantly reduced the crystallinity of raw hydroxyapatite, and made the stability of crystal structure decreased. Thus, the material may have higher solubility, benefitting for the faster release of calcium/phosphorus ions.

Example 2

ε-Aminocaproic acid, alanine, phenylalanine, proline, hydroxyproline, lysine, calcium citrate, and hydroxyapatite were respectively taken out 122.5 g, 0.9 g, 0.8 g, 1.2 g, 4 g, 1.5 g, 10.5 g, 54.3 g, and added to 250 ml three-necked bottle, following by addition of 70 ml distilled water, to which nitrogen was purged for protection. Under stirring, the mixture was gradually warmed to 150-200° C. and slowly dehydrated, and then continued to gradually heat to 210° C. for melting, and at 220° C., the in situ polymerization and complex reaction was successively carried out for 3.5 h and ceased. Under the protection of nitrogen, the reaction mixture was cooled to ambient temperature, to obtain bone repair materials of multivariant amino acid polymer-modified hydroxyapatite, with a yield of 91.2%. The obtained composite material was crushed into particles with diameter 1-5 mm, and the content of inorganic substance was detected by burning at 800° C. The total content of calcium/phosphorus salts in composite materials was 36%, in which the content of calcium citrate was 5.2%, and the content of hydroxyapatite was 30.8%.

Above granular composite material was injection-molded as normal sample belt at a temperature of 160-250° C. and under a pressure of 60-150 MPa. The compressive strength of standard sample belt was measured as 145 MPa, and the bending strength as 89 MPa. Under said injection-moulding conditions, the composite material was injection-molded into the lumbar vertebrae support of 24×12×10, with a compressive strength of up to 10890 N (3 mm deformation).

The supportive complex bone implant of multivariant amino acid polymer-modified hydroxyapatite was subjected to degradation and bioactive test in simulated body fluid, using the supportive complex implant of multivariant amino acid polymer-hydroxyapatite containing a same ratio of hydroxyapatite as reference. After soaking for 12 weeks, the calcium ion concentration of experimental sample was 2.7 times that of the reference, while the phosphorus ion concentration of experimental sample was 2.5 times that of the reference; analysis of superficial deposit showed that after the experimental sample was soaked for three days, the surface of sample was covered by apatite sediments, but for the reference, it was seven days. For the degradation, after the experimental sample was soaked for 12 weeks, the experimental sample lost 5.5% of total weight in previous four weeks, then it maintained stable. After becoming stable, the compressive strength remained 88%, fully complying with the replacement and repair requirements of chest/lumbar vertebrae for human body.

Example 3

ε-Aminocaproic acid, alanine, phenylalanine, proline, hydroxyproline, lysine, calcium sulphate dihydrate, and hydroxyapatite were respectively taken out 122.5 g, 0.9 g, 0.8 g, 1.2 g, 4 g, 4.8 g, 12.2 g, 60 g, and added to 250 ml three-necked bottle, following by addition of 70 ml distilled water, to which nitrogen was purged for protection. Under stirring, the mixture was gradually warmed to 150-200° C. and slowly dehydrated, and then continued to gradually heat to 210° C. for melting, and at 220° C., the in situ polymerization and complex reaction was successively carried out for 3.5 h and ceased. Under the protection of nitrogen, the reaction mixture was cooled to ambient temperature, to obtain bone repair materials of multivariant amino acid polymer-modified hydroxyapatite, with a yield of 91.2%. The obtained composite material was crushed into particles with diameter 1-5 mm, and the content of inorganic substance was detected by burning at 800° C. The total content of inorganic salts in composite materials was 37.5%, in which the content of calcium sulphate was 5.2%, and the content of hydroxyapatite was 32.3%.

Above granular composite material was injection-molded as normal sample belt at a temperature of 160-250° C. and under a pressure of 60-150 MPa. The compressive strength of standard sample belt was measured as 142 MPa, and the bending strength as 87 MPa. Under said injection-moulding conditions, the composite material was injection-molded into the lumbar vertebrae support of 24×12×10, with a compressive strength of up to 11470 N (3 mm deformation).

The supportive complex bone implant of multivariant amino acid polymer-modified hydroxyapatite was soaked for 12 weeks in simulated body fluid, and lost 7.5% of total weight in previous four weeks, then it maintained stable. After becoming stable, the compressive strength remained 86%, fully complying with the replacement and repair requirements of chest/lumbar vertebrae for human body.

Example 4

ε-Aminocaproic acid, alanine, phenylalanine, proline, hydroxyproline, lysine, calcium sulphate dihydrate, and hydroxyapatite were respectively taken out 78.6 g, 8.9 g, 16.5 g, 5.8 g, 6.6 g, 14.6 g, 12.5 g, 56.5 g, and added to 250 ml three-necked bottle, following by addition of 70 ml distilled water, to which nitrogen was purged for protection. Under stirring, the mixture was gradually warmed to 150-200° C. and slowly dehydrated, and then continued to gradually heat to 210° C. for melting, and at 220° C., the in situ polymerization and complex reaction was successively carried out for 3.5 h and ceased. Under the protection of nitrogen, the reaction mixture was cooled to ambient temperature, to obtain bone repair materials of multivariant amino acid polymer-modified hydroxyapatite, with a yield of 90.9%. The obtained composite material was crushed into particles with diameter 1-5 mm, and the content of inorganic substance was detected by burning at 800° C. The total content of inorganic salts in composite materials was 37%, in which the content of calcium sulphate was 5.5%, and the content of hydroxyapatite was 31.5%.

Above granular composite material was injection-molded as normal sample belt at a temperature of 160-250° C. and under a pressure of 60-150 MPa. The compressive strength of standard sample belt was measured as 130 MPa, and the bending strength as 72 MPa. Under said injection-moulding conditions, the composite material was injection-molded into the lumbar vertebrae support of 24×12×10, with a compressive strength of up to 8900 N (3 mm deformation).

The supportive complex bone implant of multivariant amino acid polymer-modified hydroxyapatite was soaked for 12 weeks in simulated body fluid, and lost 10.5% of total weight in previous four weeks, then it maintained stable. After becoming stable, the compressive strength remained 82%, fully complying with the replacement and repair requirements of chest/lumbar vertebrae for human body.

Example 5

ε-Aminocaproic acid, alanine, phenylalanine, proline, hydroxyproline, lysine, calcium hydrogen phophate, and hydroxyapatite were respectively taken out 122.5 g, 0.9 g, 0.8 g, 1.2 g, 4 g, 1.5 g, 11.7 g, 70.1 g, and added to 250 ml three-necked bottle, following by addition of 70 ml distilled water, to which nitrogen was purged for protection. Under stirring, the mixture was gradually warmed to 150-200° C. and slowly dehydrated, and then continued to gradually heat to 210° C. for melting, and at 220° C., the in situ polymerization and complex reaction was carried out for 3.5 h and ceased. Under the protection of nitrogen, the reaction mixture was cooled to ambient temperature, to obtain bone repair materials of multivariant amino acid polymer-modified hydroxyapatite, with a yield of 91.5%. The obtained composite material was crushed into particles with diameter 1-5 mm, and the content of inorganic substance was detected by burning at 800° C. The total content of inorganic salts in composite materials was 42%, in which the content of calcium sulphate was 6%, and the content of hydroxyapatite was 36%.

Above granular composite material was injection-molded as normal sample belt at a temperature of 160-250° C. and under a pressure of 60-150 MPa. The compressive strength of standard sample belt was measured as 140 MPa, and the bending strength as 82 MPa. Under said injection-moulding conditions, the composite material was injection-molded into the lumbar vertebrae support of 24×12×10, with a compressive strength of up to 9950 N (3 mm deformation).

The supportive complex bone implant of multivariant amino acid polymer-modified hydroxyapatite was soaked for 12 weeks in simulated body fluid, and lost 3.5% of total weight in previous four weeks, then it maintained stable.

After becoming stable, the compressive strength remained 89%, fully complying with the replacement and repair requirements of chest/lumbar vertebrae for human body.

Example 6

ε-Aminocaproic acid, alanine, phenylalanine, proline, hydroxyproline, lysine, calcium sulphate dihydrate, and hydroxyapatite were respectively taken out 122.5 g, 0.9 g, 0.8 g, 1.2 g, 4 g, 1.5 g, 11.4 g. 58.7 g, and added to 250 ml three-necked bottle, following by addition of 70 ml distilled water, to which nitrogen was purged for protection. Under stirring, the mixture was gradually warmed to 150-200° C. and slowly dehydrated, and then continued to heat to 210° C. for melting, and at 220° C., the in situ polymerization and complex reaction was carried out for 3.5 h and ceased. Under the protection of nitrogen, the reaction mixture was cooled to ambient temperature, to obtain bone repair materials of multivariant amino acid polymer-modified hydroxyapatite, with a yield of 90.9%. The obtained composite material was crushed into particles with diameter 1-5 mm, and the content of inorganic substance was detected by burning at 800° C. The total content of inorganic salts in composite materials was 37.5%, in which the content of calcium sulphate was 5%, and the content of hydroxyapatite was 32.5%.

Above granular composite material was injection-molded as normal sample belt at a temperature of 160-250° C. and under a pressure of 60-150 MPa. The compressive strength of standard sample belt was measured as 143 MPa, and the bending strength as 89 MPa. Under said injection-moulding conditions, the composite material was injection-molded into the lumbar vertebrae support of 16×13×9, with a compressive strength of up to 9835 N (3 mm deformation).

The supportive complex bone implant of multivariant amino acid polymer-modified hydroxyapatite was soaked for 12 weeks in simulated body fluid, and lost 7% of total weight in previous four weeks, then it maintained stable. After becoming stable, the compressive strength remained 87%, fully complying with the replacement and repair requirements of chest/lumbar vertebrae for human body.

Example 7

ε-Aminocaproic acid, alanine, phenylalanine, proline, hydroxyproline, lysine, calcium sulphate dihydrate, and hydroxyapatite were respectively taken out 122.5 g, 0.9 g, 0.8 g, 1.2 g, 4 g, 1.5 g, 9.9 g, 53 g, and added to 250 ml three-necked bottle, following by addition of 70 ml distilled water, to which nitrogen was purged for protection. Under stirring, the mixture was gradually warmed to 150-200° C. and slowly dehydrated, and then continued to heat to 210° C. for melting, and at 220° C., the in situ polymerization and complex reaction was carried out for 3.5 h and ceased. Under the protection of nitrogen, the reaction mixture was cooled to ambient temperature, to obtain bone repair materials of multivariant amino acid polymer-modified hydroxyapatite, with a yield of 90.6%. The obtained composite material was crushed into particleswith diameter 1-5 mm, and the content of inorganic substance was detected by burning at 800° C. The total content of inorganic salts in composite materials was 35%, in which the content of calcium sulphate was 4.5%, and the content of hydroxyapatite was 30.5%.

Above granular composite material was injection-molded as normal sample belt at a temperature of 160-250° C. and under a pressure of 60-150 MPa. The compressive strength of standard sample belt was measured as 145 MPa, and the bending strength as 90 MPa. Under said injection-moulding conditions, the composite material was injection-molded into the lumbar vertebrae support of 26×12×10, with a compressive strength of up to 11980 N (3 mm deformation).

The supportive complex bone implant of multivariant amino acid polymer-modified hydroxyapatite was soaked for 12 weeks in simulated body fluid, and lost 6% of total weight in previous four weeks, then it maintained stable. After becoming stable, the compressive strength remained 87%, fully complying with the replacement and repair requirements of chest/lumbar vertebrae for human body.

Example 8

ε-Aminocaproic acid, alanine, phenylalanine, proline, hydroxyproline, lysine, calcium sulphate dihydrate, and hydroxyapatite were respectively taken out 122.5 g, 0.9 g, 0.8 g, 1.2 g, 4 g, 1.5 g, 8.4 g, 46.5 g, and added to 250 ml three-necked bottle, following by addition of 70 ml distilled water, to which nitrogen was purged for protection. Under stirring, the mixture was gradually warmed to 150-200° C. and slowly dehydrated, and then continued to heat to 210° C. for melting, and at 220° C., the in situ polymerization and complex reaction was carried out for 3.5 h and ceased. Under the protection of nitrogen, the reaction mixture was cooled to ambient temperature, to obtain bone repair materials of multivariant amino acid polymer-modified hydroxyapatite, with a yield of 90.2%. The obtained composite material was crushed into particles of with diameter 1-5 mm, and the content of inorganic substance was detected by burning at 800° C. The total content of inorganic salts in composite materials was 32%, in which the content of calcium sulphate was 4%, and the content of hydroxyapatite was 28%.

Above granular composite material was injection-molded as normal sample belt at a temperature of 160-250° C. and under a pressure of 60-150 MPa. The compressive strength of standard sample belt was measured as 147 MPa, and the bending strength as 95 MPa. Under said injection-moulding conditions, the composite material was injection-molded into the lumbar vertebrae support of 24×12×8, with a compressive strength of up to 13670 N (3 mm deformation). The supportive complex bone implant of multivariant amino acid polymer-modified hydroxyapatite was soaked for 12 weeks in simulated body fluid, and lost 5% of total weight in previous four weeks, then it maintained stable. After becoming stable, the compressive strength remained 89%, fully complying with the replacement and repair requirements of chest/lumbar vertebrae for human body.

Example 9

ε-Aminocaproic acid, alanine, phenylalanine, proline, hydroxyproline, lysine, calcium hydrogen phosphate, and hydroxyapatite were respectively taken out 122.5 g, 0.9 g, 0.8 g, 1.2 g, 4 g, 1.5 g, 7.7 g, 50.5 g, and added to 250 ml three-necked bottle, following by addition of 70 ml distilled water, to which nitrogen was purged for protection. Under stirring, the mixture was gradually warmed to 150-200° C. and slowly dehydrated, and then continued to heat to 210° C. for melting, and at 220° C., the in situ polymerization and complex reaction was carried out for 3.5 h and ceased. Under the protection of nitrogen, the reaction mixture was cooled to ambient temperature, to obtain bone repair materials of multivariant amino acid polymer-modified hydroxyapatite, with a yield of 90.5%. The obtained composite material was crushed into particles with diameter 1-5 mm, and the content of inorganic substance was detected by burning at 800° C. The total content of inorganic salts in composite materials was 32%, in which the content of calcium hydrogen phosphate was 4.5%, and the content of hydroxyapatite was 29.5%.

Above granular composite material was injection-molded as normal sample belt at a temperature of 160-250° C. and under a pressure of 60-150 MPa. The compressive strength of standard sample belt was measured as 143 MPa, and the bending strength as 95 MPa. Under said injection-moulding conditions, the composite material was injection-molded into the lumbar vertebrae support of 24×12×10, with a compressive strength of up to 11800 N (3 mm deformation).

The supportive complex bone implant of multivariant amino acid polymer-modified hydroxyapatite was subjected to degradation and bioactive test in simulated body fluid, using the supportive complex implant of multivariant amino acid polymer-hydroxyapatite containing a same ratio of hydroxyapatite as reference. After soaking for 12 weeks, the calcium ion concentration of experimental sample was 1.6 times that of the control, while the phosphorus ion concentration of experimental sample was 1.3 times that of the reference. The experimental sample lost 5.5% of total weight in previous four weeks, then it maintained stable. After becoming stable, the compressive strength remained 90%, fully complying with the replacement and repair requirements of cervical vertebrae for human body.

Example 10

ε-Aminocaproic acid, alanine, phenylalanine, proline, hydroxyproline, lysine, calcium hydrogen phosphate, and hydroxyapatite were respectively taken out 122.5 g, 0.9 g, 0.8 g, 1.2 g, 4 g, 1.5 g, 9.1 g, 60.1 g, and added to 250 ml three-necked bottle, following by addition of 70 ml distilled water, to which nitrogen was purged for protection. Under stirring, the mixture was gradually warmed to 150-200° C. and slowly dehydrated, and then continued to heat to 210° C. for melting, and at 220° C., the in situ polymerization and complex reaction was carried out for 3.5 h and ceased. Under the protection of nitrogen, the reaction mixture was cooled to ambient temperature, to obtain bone repair materials of multivariant amino acid polymer-modified hydroxyapatite, with a yield of 91.0%. The obtained composite material was crushed into particles with diameter 1-5 mm, and the content of inorganic substance was detected by burning at 800° C. The total content of inorganic salts in composite materials was 38%, in which the content of calcium hydrogen phosphate was 5%, and the content of hydroxyapatite was 33%.

Above granular composite material was injection-molded as normal sample belt at a temperature of 160-250° C. and under a pressure of 60-150 MPa. The compressive strength of standard sample belt was measured as 141 MPa, the bending strength as 87 MPa. Under said injection-moulding conditions, the composite material was injection-molded into the cervical vertebrae support of 14×11×9, with a compressive strength of up to 7857 N (3 mm deformation).

The supportive complex bone implant of multivariant amino acid polymer-modified hydroxyapatite was soaked in simulated body fluid for 12 weeks. The calcium ion concentration of experimental sample was 2.2 times that of the control, while the phosphorus ion concentration of experimental sample was 2.5 times that of the reference. The experimental sample lost 2.5% of total weight in previous four weeks, then it maintained stable. After becoming stable, the compressive strength remained 90%, fully complying with the replacement and repair requirements of skull for human body.

Comparative Example 1

ε-Aminocaproic acid, alanine, phenylalanine, proline, hydroxyproline, lysine, calcium citrate, and hydroxyapatite were respectively taken out 122.5 g, 0.9 g, 0.8 g, 1.2 g, 4 g, 1.5 g, 26.2 g, 60.1 g, and added to 250 ml three-necked bottle, following by addition of 70 ml distilled water, to which nitrogen was purged for protection. Under stirring, the mixture was gradually warmed to 150-200° C. and slowly dehydrated. After completion of dehydration, the mixture was then continued to heat to 210° C. for melting, and at 220° C., the in situ polymerization and complex reaction was carried out for 3.5 h and ceased. Under the protection of nitrogen, the reaction mixture was cooled to ambient temperature, with a yield of 91.0%. The obtained composite material was crushed into particles with diameter 1-5 mm, and the content of inorganic substance was detected by burning at 800° C. The total content of inorganic salts in composite materials was 41%, in which the content of calcium hydrogen phosphate was 11%, and the content of hydroxyapatite was 30%.

Above composite material was injection-molded as normal sample belt at a temperature of 160-250° C. and under a pressure of 60-150 MPa. The compressive strength of standard sample belt was measured as 152 MPa, and the bending strength as 96 MPa. Under said injection-moulding conditions, the composite material was injection-molded into the cervical vertebrae support of 14×11×9, with a compressive strength of up to 8965 N (3 mm deformation).

The supportive complex bone implant of multivariant amino acid polymer-modified hydroxyapatite (Experimental sample) was subjected to degradation and bioactive test in simulated body fluid, using the complex material of multivariant amino acid polymer-hydroxyapatite reported in the Chinese invention publication (No. CN101417149) as reference. Analysis of superficial deposit showed that after the experimental sample was soaked for five days, the surface of sample was covered by sediments apatite, but for the reference, it was 14 days. After both of normal mechanical sample belts was soaked for 12 weeks, the compressive strength of experimental sample reduced by 10%, and the bending strength reduced by 13%; while the compressive strength of reference sample reduced by 36%, and the bending strength reduced by 40%, indicating that the rapid releasing of calcium ions and phosphorus ions is beneficial for the deposition of surface apatites of bond implant according to the present invention, and during soaking, the strength less declined.

Comparative Example 2

Compact bone of four-year adult cattle was chosen, washed, dried in the air, and processed into 22×10×10 of vertebral body support. Under the same conditions, the compressive strength was tested to be 9498 N (3 mm deformation).

Said support of cattle bone was soaked in simulated body fluid for 12 weeks, with 15% of weight loss. After becoming stable, the compressive strength remained 75% and faster decreased in soaking solution.

Comparative Example 3

Compact bone of four-year adult cattle was chosen, washed, dried in the air, and processed into 14×11×9 of cervical vertebral support. Under the same conditions, the compressive strength was tested to be 6580 N (3 mm deformation).

Said support of cattle bone was soaked in simulated body fluid for 12 weeks, with 15% of weight loss. After becoming stable, the compressive strength remained 77.5% and faster decreased in soaking solution.

Comparative Example 4

Metal titanium was chosen, and titanium support (22× 10×10) was soaked in simulated body fluid for 12 weeks, with 0% of weight loss and without change. The surface did not show biological activity.

The invention claimed is:

1. A bone repair material, comprising a multivariant amino acid polymer having ε-aminocaproic acid, one or more α-amino acids, and a modified hydroxyapatite,
    wherein the modified hydroxyapatite comprises a pharmaceutically acceptable calcium salt and hydroxyapatite,
    wherein a mass ratio of the calcium salt to hydroxyapatite is 2:98 to 20:80,
    wherein a mass percentage of the modified hydroxyapatite is 10-70% based on a total mass of the bone repair material, and
    wherein a molar percentage of ε-aminocaproic acid in the multivariant amino acid polymer is 60-99% based on a total molar quantity of amino acids in the multivariant amino acid polymer.

2. The bone repair material according to claim 1, wherein the pharmaceutically acceptable calcium salt molecule resides in a crystal lattice of hydroxyapatite.

3. The bone repair material according to claim 1, wherein the pharmaceutically acceptable calcium salt is selected from the group of calcium hydrogen phosphate, calcium biphosphate, calcium sulfate, calcium citrate, calcium glycerophosphate, and mixtures thereof.

4. A supportive bone repair implant, comprising the bone repair material according to claim 1, having a compressive strength of 95-150 MPa, and a bending strength of 70-130 MPa.

5. The bone repair material according to claim 1, wherein the mass ratio of the calcium salt to hydroxyapatite is 5:95 to 15:85.

6. The bone repair material according to claim 1, wherein the mass percentage of the modified hydroxyapatite is 25-55% based on the total mass of the bone repair material.

* * * * *